(12) United States Patent
Mayer et al.

(10) Patent No.: US 8,408,050 B2
(45) Date of Patent: Apr. 2, 2013

(54) METHOD FOR MEASURING A FLUID COMPOSITION PARAMETER BY MEANS OF A FLOW SENSOR

(75) Inventors: Felix Mayer, Stäfa (CH); Mark Hornung, Männedorf (CH); Samuel Wehrli, Zürich (CH)

(73) Assignee: Sensirion AG, Stafa (CH)

( * ) Notice: Subject to any disclaimer, the term of this patent is extended or adjusted under 35 U.S.C. 154(b) by 677 days.

(21) Appl. No.: 12/583,747

(22) Filed: Aug. 25, 2009

(65) Prior Publication Data

US 2010/0089118 A1 Apr. 15, 2010

(30) Foreign Application Priority Data

Oct. 9, 2008 (EP) ..................... 08017691

(51) Int. Cl.
*G01N 25/00* (2006.01)
*G01F 1/68* (2006.01)

(52) U.S. Cl. ..................... 73/61.76; 73/61.46; 73/204.19

(58) Field of Classification Search ............... 73/1.34, 73/23.21, 25.01, 204.18, 204.19, 61.46, 61.76, 73/861.03; 702/24, 25, 100
See application file for complete search history.

(56) References Cited

U.S. PATENT DOCUMENTS

| | | | |
|---|---|---|---|
| 4,373,386 A | 2/1983 | Schuddemat et al. |
| 4,501,145 A | 2/1985 | Boegli et al. |
| 4,693,116 A | 9/1987 | Miura et al. |
| 4,712,996 A | 12/1987 | Adams et al. |
| 4,885,938 A | 12/1989 | Higashi |
| 4,909,078 A | 3/1990 | Sittler et al. |
| 4,961,348 A | 10/1990 | Bonne |
| 5,237,523 A | 8/1993 | Bonne et al. |
| 5,339,687 A | 8/1994 | Gimson et al. |
| 5,404,753 A | 4/1995 | Hecht et al. |
| 5,460,841 A | 10/1995 | Herdeman |
| 5,515,295 A | 5/1996 | Wang |
| 5,515,714 A | 5/1996 | Sultan et al. |
| 5,533,412 A | 7/1996 | Jerman et al. |
| 5,596,219 A | 1/1997 | Hierold |
| 5,804,720 A | 9/1998 | Morimasa et al. |

(Continued)

FOREIGN PATENT DOCUMENTS

| | | |
|---|---|---|
| DE | 10129300 | 6/2000 |
| EP | 1426740 | 11/2002 |

(Continued)

OTHER PUBLICATIONS

"Amminex, Ammonia and Hydrogen Enabling Technologies", Press Release, Copenhagen, Dec. 21, 2009, 1 Page.

(Continued)

*Primary Examiner* — Peter Macchiarolo
*Assistant Examiner* — Jamar Ray
(74) *Attorney, Agent, or Firm* — Cooper & Dunham LLP

(57) ABSTRACT

The flow of a fluid of unknown composition is measured by leading the fluid over a first temperature sensor, a heater and a second temperature sensor. The temperature difference DTP between the temperature sensors is measured, as well as the temperature T of at least one of them. In addition, calibration data is used to store the temperature Tref of a known reference fluid. The offset T−Tref at a given temperature difference DTP is a direct measure of the composition of the fluid and allows to retrieve any parameter depending on the same.

11 Claims, 2 Drawing Sheets

U.S. PATENT DOCUMENTS

| | | | |
|---|---|---|---|
| 5,830,372 | A | 11/1998 | Hierold |
| 5,980,102 | A | 11/1999 | Stulen et al. |
| 6,209,402 | B1 | 4/2001 | Yamada |
| 6,349,596 | B1 | 2/2002 | Nakada et al. |
| 6,650,325 | B1 | 11/2003 | Voorhies et al. |
| 6,662,121 | B1 | 12/2003 | Oda et al. |
| 6,782,743 | B2 | 8/2004 | Koike et al. |
| 6,920,786 | B2 | 7/2005 | Mayer et al. |
| 7,188,519 | B2 * | 3/2007 | Hornung et al. ........... 73/204.26 |
| 2004/0099057 | A1 | 5/2004 | Hornung et al. |
| 2006/0026949 | A1 | 2/2006 | Takahata et al. |
| 2007/0144151 | A1 | 6/2007 | Lueders et al. |
| 2007/0241093 | A1 | 10/2007 | von Waldkirch et al. |
| 2008/0066453 | A1 | 3/2008 | Oberski et al. |
| 2009/0028845 | A1 | 1/2009 | Maes et al. |
| 2009/0123361 | A1 | 5/2009 | Johannessen et al. |
| 2009/0249869 | A1 | 10/2009 | Meier et al. |
| 2010/0021780 | A1 | 1/2010 | Johannessen et al. |
| 2010/0024403 | A1 | 2/2010 | Johannessen et al. |
| 2010/0047638 | A1 | 2/2010 | Johannessen |

FOREIGN PATENT DOCUMENTS

| | | |
|---|---|---|
| EP | 1772717 | 4/2007 |
| EP | 1840535 | 10/2007 |
| WO | WO0118500 | 3/2001 |
| WO | WO0198736 | 12/2001 |
| WO | WO2006081824 | 8/2006 |
| WO | WO2007000170 | 1/2007 |

OTHER PUBLICATIONS

"VDI Conference on NOx Control", Nürnberg, Germany, Jul. 1, 2009. Presentation by Dr. Tue Johannessen: "Compact Amonia Storage for SCR Nox Control", pp. 1-28.

"Solid Ammonia as Energy Carrier: Current Status and Future Prospects", by Debasish Chakraborty et al, published on Fuel Cells Bulletin, Oct. 2009, pp. 12-15.

"Commercial Vehicle Diesel Engines with Exhaust Gas Aftertreatment: Daimler Chrysler Develops the Next Generation of SCR Technology", Edith Meissner, 8 pages, May 4, 2004 (English and German Versions).

U.S. Appl. No. 12/653,490, filed Dec. 15, 2009.

* cited by examiner

METHOD FOR MEASURING A FLUID COMPOSITION PARAMETER BY MEANS OF A FLOW SENSOR

CROSS REFERENCE TO RELATED APPLICATIONS

This application claims the priority of European patent application 08017691.0, filed Oct. 9, 2008, the disclosure of which is incorporated herein by reference in its entirety.

BACKGROUND OF THE INVENTION

The invention relates to a method for measuring a parameter depending on the composition of an unknown fluid by means of a flow sensor, in particular by means of a thermal flow sensor comprising a heater arranged between two temperature sensors.

EP 1 426 740 describes a method for measuring a material-dependent parameter, such as a mixture ratio, of a fluid by means of a flow sensor. The fluid is led over a first temperature sensor, a heater and then a second temperature sensor. The temperature difference between the first and the second sensor as well as the temperature of the second sensor are measured. The mixture ratio of the fluid is then calculated by various, fairly complex mathematical transformations.

BRIEF SUMMARY OF THE INVENTION

Hence, it is a general object of the invention to provide a method of the type mentioned above that allows to measure a parameter depending on the composition of an unknown fluid that obviates the need for complicated mathematical transformations.

This problem is solved by a method for measuring a parameter depending on the composition of an unknown fluid by means of a flow sensor, wherein said flow sensor comprises a heater arranged between a first and a second temperature sensor, said method comprising the steps of leading said unknown fluid over said first temperature sensor, said heater and said second temperature sensor, measuring a temperature difference DTP between a temperature TP2 at said second temperature sensor and a temperature TP1 at said first temperature sensor as well as a single temperature T, which single temperature is equal to $(k1 \times TP1) + (k2 \times TP2)$ with $k1 \neq -k2$ retrieving first calibration data, which first calibration data was obtained from a calibration measurement carried out with a reference fluid of known composition, and which first calibration data is such that it allows to calculate the value of the single temperature that the reference fluid exhibited at a given temperature difference, using said first calibration data to calculate a reference temperature Tref(DTP) equal to the single temperature of said reference fluid at said temperature difference DTP, and deriving said parameter from a temperature offset $D=T-Tref(DTP)$ between said single temperature T measured for said unknown fluid at said temperature difference DTP and the single temperature of said reference fluid at said temperature difference DTP.

Accordingly, as in the prior art, the unknown fluid is led over the first temperature sensor, then the heater, and finally the second temperature sensor.

"The difference $DTP = TP2-TP1$ between the temperature TP2 at the second temperature sensor and the temperature TP1 at the first temperature sensor is measured, as well as a "single temperature T". The single temperature T is equal to $(k1 \times TP1) + (k2 \times TP2)$ with $k1 \neq -k2$. Advantageously $T = TP1$ or $T = TP2$ is used for computational simplicity, but any linear combination of the two temperatures can be used."

Now, "first calibration data" is retrieved, e.g. from a memory. This first calibration data was obtained from a calibration measurement carried out with a reference fluid of known composition. The first calibration data is such that it allows to calculate the value of the single temperature that the reference fluid exhibited at a given temperature difference, and in particular at the temperature difference DTP measured for the unknown fluid. This single temperature of the reference fluid at DTP is called the "reference temperature Tref (DTP)".

In a next step, the "temperature offset" $D=T-Tref(DTP)$ is calculated, i.e. the difference between the single temperature T measured for the unknown fluid and the single temperature of the reference fluid at the measured temperature difference DTP.

As it has been found, the temperature offset D is a direct measure of the composition of the unknown fluid, independent of the temperature difference DTP and therefore independent of the flow of the fluid. Hence, the temperature offset D can be used to easily calculate the desired parameter, e.g. by means of a lookup-table that contains the data required for calculating the parameter from the temperature offset D.

Since the temperature offset D does not depend on the flow but merely on the composition of the fluid, the present method can be used to determine the parameter at any non-zero flow as well as for zero flow without requiring any flow-dependent corrections.

In a typical application, the unknown fluid is a mixture of two known fluids and the parameter to be determined from the temperature offset D is the mixture ratio of the two fluids.

The present invention can be used for determining a composition-dependent parameter of any type of fluid, in particular of liquids as well as of gases.

BRIEF DESCRIPTION OF THE DRAWINGS

The invention will be better understood and objects other than those set forth above will become apparent when consideration is given to the following detailed description thereof. Such description makes reference to the annexed drawings, wherein.

DETAILED DESCRIPTION OF THE INVENTION

Definitions

The term "unknown fluid" designates the fluid whose composition is not known. For example, the unknown fluid is a mixture of two known fluids with unknown mixture ratio.

The term "fluid temperature TF" designates the temperature of the fluid in the absence of any heating contribution by the heater, e.g. a temperature measured at a fairly large distance before the heater.

Note Regarding FIGS. 4-8:

Each of the diagrams of FIGS. 4-8 shows seven different curves. These curves correspond to measurements with a fluid of varying composition. In the specific example shown here, the fluid was air mixed with C4H10. The bottommost curve of each diagram corresponds to a measurement where the content of C4H10 was 0%, the second curve from the bottom corresponds to a fluid with a C4H10-content of 10%, the third curve to a fluid with a C4H10-content of 20%, etc., with the topmost curve corresponding to a fluid with a C4H10-content of 60%.

Figure 4:
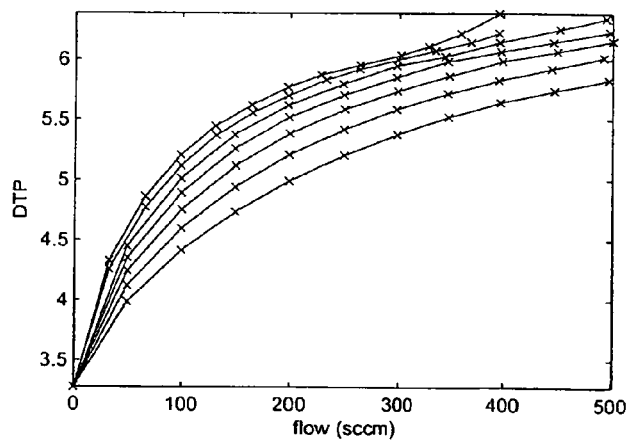
FIG. 4 shows the dependence of the temperature difference DTP on the flow of the fluid for differing fluid compositions.

The temperatures in FIGS. 4-8 are in arbitrary units. In FIG. 4, DTP=3.25 corresponds to a temperature difference of 0° C.

Figure 1:
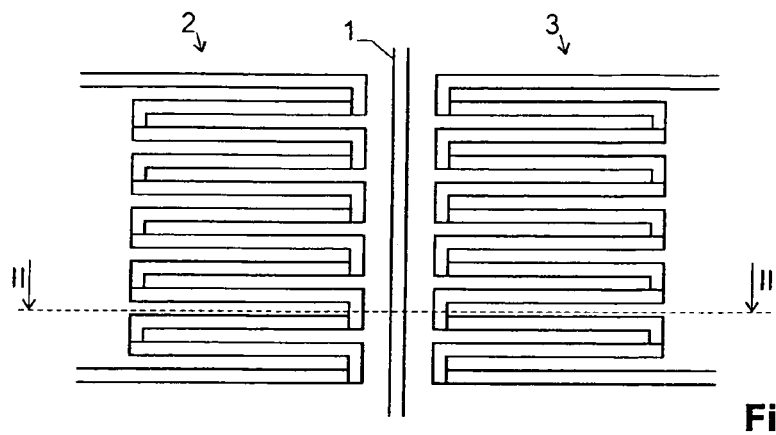
FIG. 1 is a top view of the heater and the temperature sensors of a flow sensor.
Figure 2:
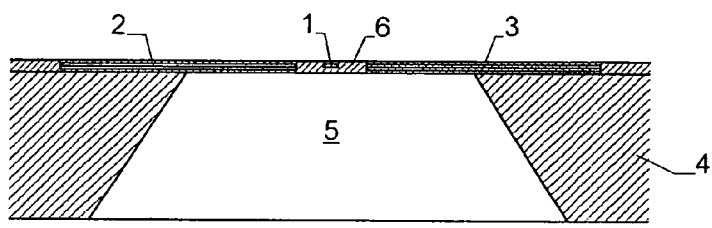
FIG. 2 is a sectional view along line II-II of FIG. 1.

The Sensor:

FIGS. 1 and 2 show an example of a thermal flow sensor comprising a heater 1 arranged between a first temperature sensor 2 and a second temperature sensor 3. In the present embodiment, the temperature sensors are thermopiles, albeit the invention can also be carried out with other types of temperature sensors, such as resistive temperature sensors. The flow sensor further comprises a substrate 4, such as a semiconductor substrate, wherein the heater 1, the temperature sensors 2, 3 as well as further components are integrated on a surface thereof. An opening or recess 5 in substrate 4 has been manufactured e.g. by anisotropic etching and is spanned by a membrane 6. The temperature sensors 2, 3 as well as the heater 1 are arranged at least partially on the membrane 6 for good thermal insulation.

This type of flow sensor is e.g. described in EP 1 426 740 and WO 01/98736. To measure the flow of a fluid, the fluid is led over first temperature sensor 2, then heater 1 and finally second temperature sensor 3. Heater 1 is heated by an electric current, advantageously to a temperature that lies at a fixed offset above the temperature of substrate 4. Thermal conductance through membrane 6 as well as through the fluid leads to a temperature increase at the inner contacts of the temperature sensors 2, 3, while the outer contacts remain at the bulk temperature of substrate 4. In the presence of a non-zero flow, however, the temperature distribution is asymmetric and the temperature TP1 measured by first temperature sensor 2 will generally be lower than the temperature TP2 measured by second temperature sensor 3.

The temperature difference DTP=TP2−TP1 between the second and the first temperatures TP2, TP1 is a measure of the flow and can be used to determine the flow.

Figure 3:
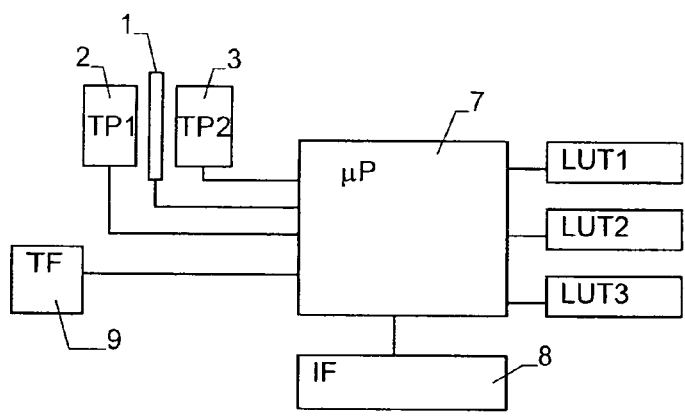
FIG. 3 is a simplified block diagram of the flow sensor.

A simple block diagram of the flow sensor is shown in FIG. 3. As can be seen, it comprises a control unit 7, which e.g. comprises analogue circuitry, such as amplifiers, an A/D-converter as well as digital circuitry. It controls heater 1 and measures the signals from the temperature sensors 2, 3. It processes the signals by accessing lookup tables LUT1, LUT2 and LUT3 in a manner described below, and has an interface 8 through which it can communicate with external circuitry.

Control unit 7 is also connected to a temperature sensor 9 measuring the fluid temperature TF.

Advantageously, all or at least part of the electronic components shown in FIG. 3 are integrated on semiconductor substrate 4, but part or all of these components may also be implemented as external circuitry.

Flow Measurement:

To measure the flow of the fluid, as mentioned, the temperature difference DTP is determined. As can be seen from FIG. 4, the relationship between the flow and the temperature difference DTP is non-linear and depends on the mixture ratio of the fluid. Therefore, control unit 7 accesses a first lookup-table LUT1, which has two input values, namely the temperature difference DTP as well as the mixture ratio of the fluid, and which provides the flow as an output value. Interpolation of the output values of lookup-table LUT1 allows to calculate the flow for any temperature difference DTP and mixture ratio.

The mixture ratio required for reading LUT1 can be obtained by the measurement procedure described in the next section.

Figure 5:
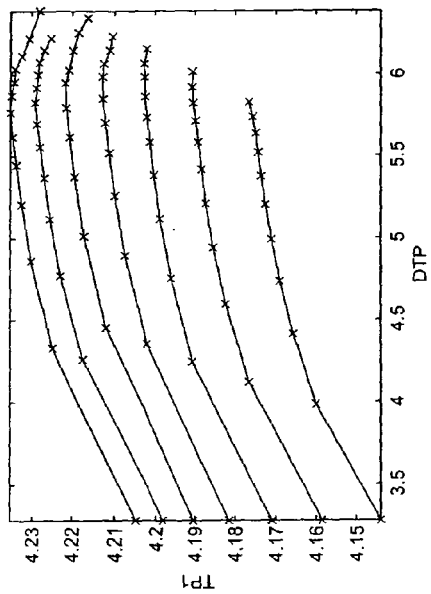
FIG. 5 shows the dependence of the second temperature TP2 on the temperature difference DTP.

Measuring the Composition:

FIG. 5 shows the dependence of temperature TP2 at second temperature sensor 3 on the temperature difference DTP for different fluid compositions. As can be seen, the curves are mutually parallel (except for deviations at high temperature differences DTP, i.e. at high flow values, where the flow starts to become turbulent).

For example, the bottommost curve, which was measured for pure air, is roughly at an offset of 0.014 (arbitrary units) below the curve above it, which was measured for a mixture of 90% air and 10% C4H10, with the offset being independent of DTP. And the third curve (measured for 80% air and 20% C4H10) is roughly 0.027 above the bottommost curve.

Hence, in the present example, the offset D=TP2$x$(DTP)−TP2air between the temperature TP2$x$ measured for a fluid of unknown mixing ratio between air and C4H10 and the temperature TP2air measured for pure air at the same temperature difference DTP depends on the mixing ratio only, but not on DTP (i.e. not on the flow).

Figure 6:
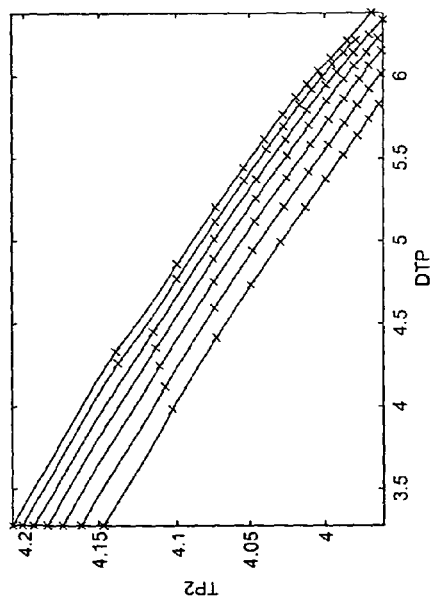
FIG. 6 shows the dependence of the offset D on the temperature difference DTP as calculated from FIG. 5.

This is illustrated by FIG. 6, which shows the offset D for the curves of FIG. 5 in respect to an earlier calibration measurement carried out with pure air. (Note: The vertical axis of FIG. 6 is scaled in 10,000 times the units of the vertical axis of FIG. 5.) As can be seen, the percentage x of C4H10 can be directly derived from the offset D using a table as follows

TABLE I

| D | x |
|---|---|
| 0 | 0% |
| 140 | 10% |
| 270 | 20% |
| 380 | 30% |
| 470 | 40% |
| 540 | 50% |
| 620 | 60% |

Hence, the mixing ratio of an unknown fluid composition can be measured by the following steps:

First, a reference measurement is made for varying flows of a fluid of known composition. This reference measurement can be used to derive the dependence of TP2ref on the temperature difference DTP. This dependence is stored as the "first calibration data", e.g. in a lookup table LUT2 of the sensor (FIG. 3).

Then, the unknown fluid is measured at a certain flow, i.e. at a certain temperature difference DTP, and the second temperature TP2(DTP) is measured. The calibration data in LUT2 is used to calculate the second temperature TP2ref (DTP) that the reference fluid had (or would have had) at the same temperature difference DTP, and the offset D=TP2(DTP)−TP2ref(DTP) is calculated.

From table I above, which may e.g. be stored as "second calibration data" in a third lookup table LUT3 of the sensor (or of a device external to the sensor), it is now possible to calculate the composition x using interpolation.

Figure 7:
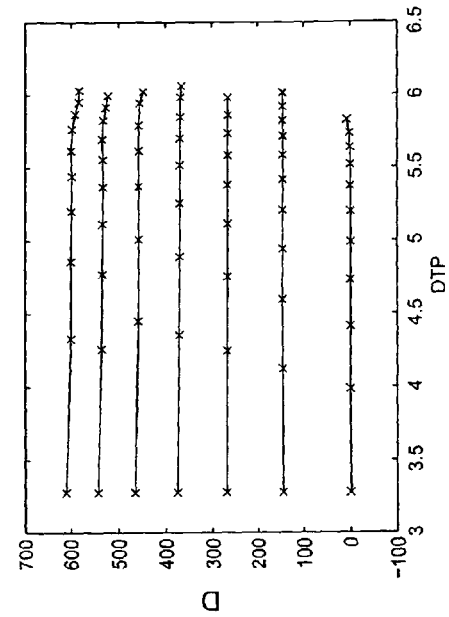
FIG. 7 shows the dependence of the first temperature TP1 on the temperature difference DTP.
Figure 8:
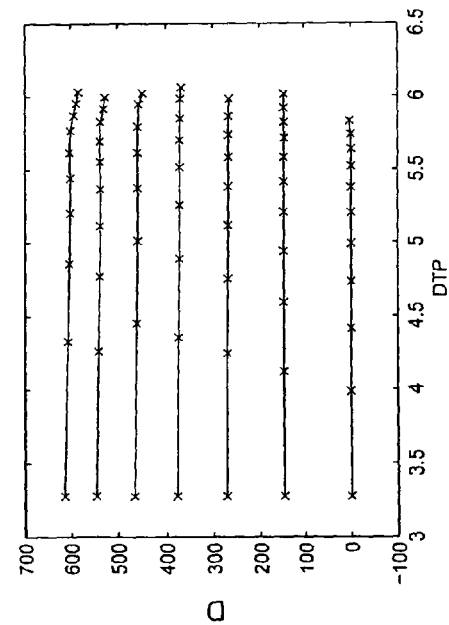
FIG. 8 shows the dependence of the offset D on the temperature difference DTP as calculated from FIG. 8.

In FIGS. 5 and 6, the second temperature TP2 has been used as "single temperature" T in the sense defined above. However, it must be noted that the same procedure can also be carried out with the first temperature TP1, as illustrated in FIGS. 7 and 8. As can be seen, the curves in FIG. 7, which show the first temperature TP1 as a function of the temperature difference DTP for air with increasing C4H10 additions, are again parallel (except for small deviations at high flow values where turbulences set it).

Hence, the same kind of calculation can be carried out for the first temperature TP1.

As mentioned above, the "single temperature" T can not only be TP1 or TP2, but also any linear combination thereof, in particular TP1+TP2. (Using T=TP1−TP2, however, makes little sense since, in this case, the offset D would be constantly 0).

Experimental evidence shows that the offset D also depends, to some slight degree, on the fluid temperature TF. Hence, advantageously, the "second calibration data" relates the temperature offset D as well as the fluid temperature TF to the mixing ratio x. For example, lookup-table LUT 3 can be a two-dimensional table having offset D and fluid temperature TF as input values.

The present method can also be used for measurements on other types of fluids, not only mixtures of air and C4H10. For example, it can be used to measure the mixture ratio of other gas compositions, as well as of liquid compositions.

Also, the parameter to be measured can be any value depending on the composition, not only the mixing ratio, by storing suitable "second calibration data".

Notes:

As mentioned above, the mixing ratio x is required for selecting the appropriate part of lookup-table LUT1 when measuring the flow of the fluid. As can be seen know, this mixing ratio can be obtained from the offset D, or, in other words, offset D may be used as an input value for retrieving the flow from lookup-table LUT1.

The lookup-tables LUT1, LUT2, LUT3 can, some or all of them, also be arranged outside the flow sensor, in external circuitry. In a particularly advantageous embodiment the offset D accessible through interface 8 such that a user of the flow sensor can perform composition-dependent operations in external circuitry.

As it has been mentioned, deviations from the described behavior start to occur when the flow of the fluid starts to become turbulent. Hence, advantageously, the temperature difference DTP and the single temperature T are measured for laminar flows.

While there are shown and described presently preferred embodiments of the invention, it is to be distinctly understood that the invention is not limited thereto but may be otherwise variously embodied and practised within the scope of the following claims.

The invention claimed is:

1. A method for determining a fluid composition parameter of an unknown fluid using a flow sensor, wherein said flow sensor comprises a heater arranged between a first and a second temperature sensor, said method comprising the steps of
   contacting said unknown fluid to said first temperature sensor, then contacting said unknown fluid to said heater, and then contacting said unknown fluid to said second temperature sensor,
   measuring a first temperature, TP1, of the unknown fluid at the first temperature sensor,
   measuring a second temperature, TP2, of the unknown fluid at the second temperature sensor,
   determining a temperature difference, DTP, between TP2 and TP1, and calculating a single temperature, T, wherein $T = (k1 \times TP1) + (k2 \times TP2)$, with $k1 \neq -k2$,
   retrieving first calibration data, wherein said first calibration data was obtained from a calibration measurement carried out with a reference fluid of known composition,
   calculating, using said first calibration data, a reference temperature, Tref(DTP), equal to a single temperature of said reference fluid for said temperature difference DTP, and
   calculating a temperature offset, D, wherein $D = T - Tref(DTP)$, and
   determining a value of the fluid composition parameter based upon the calculated value of D,
      wherein the step of determining the value of the fluid composition parameter comprises the step of referring to second calibration data which provides a corresponding value of the fluid composition parameter for the calculated value of the temperature offset D.

2. The method of claim 1 wherein said single temperature T is equal to said first temperature measured by said first temperature sensor.

3. The method of claim 1 wherein said single temperature T is equal to said second temperature measured by said second temperature sensor.

4. The method of claim 1 wherein said second calibration data also relates a fluid temperature, TF, to said parameter.

5. The method of claim 1 wherein the step of determining the value of said parameter comprises calculating the parameter as a function of said temperature offset D and a fluid temperature TF.

6. The method of claim 1 wherein said unknown fluid is a mixture of two known fluids and wherein said parameter is a mixture ratio of said known fluids.

7. The method of claim 1 wherein said flow sensor comprises a substrate having an opening or recess and a membrane arranged over said opening or recess, and wherein said temperature sensors and said heater are arranged at least partially on said membrane.

8. The method of claim 1 wherein said temperature difference DTP and said single temperature T are measured at non-zero flow of said unknown fluid.

9. The method of claim 1 wherein said temperature difference DTP and said single temperature T are measured for a laminar flow of said unknown fluid.

10. The method of claim 1 wherein said flow sensor comprises an interface to external circuitry and said method comprises the step of accessing second calibration data said first calibration data through said interface.

11. A method for determining a fluid composition parameter of an unknown fluid using a flow sensor, wherein said flow sensor comprises a heater arranged between a first and a second temperature sensor, said method comprising the steps of
   contacting said unknown fluid to said first temperature sensor, then contacting said unknown fluid to said heater, and then contacting said unknown fluid to said second temperature sensor,
   measuring a first temperature, TPI, of the unknown fluid at the first temperature sensor,
   measuring a second temperature, TP2, of the unknown fluid at the second temperature sensor, determining a temperature difference, DTP, between TP2 and TP1, and calculating a single temperature, T, wherein $T = (k1 \times TP1) + (k2 \times TP2)$, with $k1 \neq -k2$, retrieving first calibration data, wherein said first calibration data was obtained from a calibration measurement carried out with a reference fluid of known composition, calculating, using said first calibration data, a reference temperature, Tref(DTP), equal to a single temperature of said reference fluid for said temperature difference DTP, and calculating a temperature offset, D, wherein $D \times T - \text{Tref}(DTP)$, and determining a value of the fluid composition parameter based upon the calculated value of D,
  wherein the step of determining the value of said parameter comprises calculating the parameter as a function of said temperature offset D and a fluid temperature TF.

* * * * *